United States Patent [19]

Stumpp et al.

[11] Patent Number: 5,082,973
[45] Date of Patent: Jan. 21, 1992

[54] PROCESS FOR THE PREPARATION OF BIS(4-CHLOROPHENYL) SULFONE

[75] Inventors: Michael Stumpp, Deidesheim; Peter Neumann, Mannheim; Heinz Eilingsfeld, Frankenthal, all of Fed. Rep. of Germany

[73] Assignee: BASF Aktiengesellschaft, Ludwigshafen, Fed. Rep. of Germany

[21] Appl. No.: 464,208

[22] Filed: Jan. 12, 1990

[30] Foreign Application Priority Data

Feb. 1, 1989 [DE] Fed. Rep. of Germany ....... 3902890

[51] Int. Cl.$^5$ ............................................ C07C 315/00
[52] U.S. Cl. ...................................................... 568/34
[58] Field of Search ........................................... 568/34

[56] References Cited

U.S. PATENT DOCUMENTS

| | | | |
|---|---|---|---|
| 2,971,985 | 2/1961 | Joly et al. | 568/64 |
| 3,355,497 | 11/1967 | Budnick | 568/34 |
| 3,415,887 | 12/1968 | Keogh et al. | 568/34 |
| 4,871,876 | 10/1989 | Schaefer et al. | 568/34 |

FOREIGN PATENT DOCUMENTS

| | | |
|---|---|---|
| 279388 | 2/1988 | European Pat. Off. . |
| 1087592 | 8/1960 | Fed. Rep. of Germany . |
| 699725 | 12/1967 | France . |

*Primary Examiner*—Mary E. Ceperley
*Attorney, Agent, or Firm*—John H. Shurtleff

[57] ABSTRACT

A process for the preparation of bis(4-chlorophenyl) sulfone, wherein sulfur trioxide, dimethyl sulfate and chlorobenzene are reacted with each in a single reaction at a temperature of from 50° to 100° C.

10 Claims, No Drawings

PROCESS FOR THE PREPARATION OF BIS(4-CHLOROPHENYL) SULFONE

The present invention relates to an improved process for the preparation of bis(4-chlorophenyl) sulfone.

Bis(4-chlorophenyl) sulfone is an important intermediate used mainly in the manufacture of aromatic polysulfones and for the synthesis of bis(4-aminophenyl) sulfone, which is required for the therapy of leprosy and for curing epoxy resins. When used for such purposes, bis(4-chlorophenyl) sulfone must show a high degree of purity.

Prior processes for the preparation of bis(4-chlorophenyl) sulfone usually involve sulfonation of chlorobenzene. Since chlorobenzene is a relatively inactive substance in sulfonation reactions, a good conversion rate can only be achieved by using reactive sulfonating agents or by carrying out the reaction under drastic conditions.

DE-A 1,087,592 discloses a process for the preparation of bis(4-chlorophenyl) sulfone by reacting chlorobenzene with a mixture of sulfur trioxide and dimethyl- or diethylpyrosulfate. According to this disclosure, dimethyl sulfate and sulfur trioxide are first reacted with each other to form the dimethyl pyrosulfate, after which a further amount of sulfur trioxide is added to form the desired reactive sulfonating complex. This is subsequently reacted with chlorobenzene in a separate reaction vessel.

The drawback of this process is that it has to be operated in two stages.

It is an object of the present invention to provide an improved and simplified process for the preparation of bis(4-chlorophenyl) sulfone which involves reacting chlorobenzene with a reactive sulfonating agent and does not suffer from the above drawback.

We have thus found a process for the preparation of bis(4-chlorophenyl) sulfone, which is characterized in that sulfur trioxide, dimethyl sulfate and chlorobenzene are reacted with each other in a single reaction at from 50° to 100° C.

The process of the invention may be carried out in the manner described below.

The process of the invention can be carried out batchwise in a stirred vessel or, preferably, continuously in reactors comprising, for example, one or more tubes. The residence time of the reaction mixture in the reactor can be controlled, for example, by filling the tubular reactor with packing elements, i.e. the residence time can be increased or decreased by varying the geometry, particle size and packing density of the packing elements. We prefer to use spherical packing elements such as are employed in packed columns for fractional distillation of mixtures, for example glass balls or steel balls inert to the reaction mixture. The diameter of such balls is usually from 0.4 to 10 mm, preferably from 1 to 5 mm. It is advantageous to use balls of a specific size.

The reaction tubes are advantageously filled with packing elements of a material which has a catalytic effect on sulfone formation, so that such elements are also effective as sulfonating catalysts. For example, the yield and the selective effect of the reaction may be improved by using packing elements comprising sintered boric acid balls or silica gel elements doped with an acid such as phosphoric, sulfuric or boric acid. Such modified silica gel is advantageously prepared by impregnating silica gel with an aqueous solution of the acid concerned followed by drying. The boric acid balls are generally sintered at a temperature of from 150° to 200° C.

When use is made of glass balls having a diameter of 4 mm, the initial residence time is found to be about 1 minute. When the reaction mixture is recycled a number of times, it becomes more viscous as the conversion rate rises and the average residence time increases to 3 minutes.

The reaction temperature is usually from 50° to 100° C. and preferably from 70° to 90° C. Although temperatures below 50° C. are possible, they are not recommended on account of their effect on reaction time and conversion rate. The reaction temperature is advantageously higher than 60° C. If the temperature is adjusted to higher than 100° C., care should be taken to ensure that the residence time in the reactor is not excessively long either by using appropriate packing elements or by suitably adjusting the pump rate. We have found that at temperatures above 80° C. the concentration of isomeric dichlorophenyl sulfones, particularly 3,4,'-bis(chlorophenyl) sulfone, in the product increases considerably. At 90° C. for example, a concentration of unwanted 3,4,'-isomer of 10% is found.

The molar ratio of sulfur trioxide to dimethyl sulfate to chlorobenzene generally ranges from 0.01:0.005:1 to 2:1:1, preferably from 0.1:0.05:1 to 1.5:0.8:1. A particularly preferred range is from 0.5:0.25:1 to 1.1:0.6:1. The system is not very sensitive to deviations from the standard composition of 1:0.5:1.

When the components are passed once through the reactor at a rate giving a residence time of from 1 to 3 minutes, the conversion rate is 57%. This can be increased to 91% conversion by continuously pumping the effluent reaction mixture back to the fixed bed of the reactor to give an average residence time of approximately 15 minutes. No advantage is gained, we have found, by first converting sulfur trioxide and dimethyl sulfate to reactive dimethyl pyrosulfate and then reacting the latter with chlorobenzene. Precipitating the product in chlorobenzene instead of aqueous sulfuric acid gives bis(4-chlorophenyl) sulfone having a purity of >99.5%.

EXAMPLES

Example 1

A vertical glass tube having a length of 90 cm and a diameter of 4 cm was packed with glass balls and heated at 70° C. 225 g (2.0 moles) of chlorobenzene, 126 g (1.0 mole) of dimethyl sulfate and 160 g (2.0 moles) of sulfur trioxide were simultaneously fed, dropwise, to the top of the tube at approximately the same rates over 30 minutes. The residence time of the reaction mixture in the packed column was 1 to 3 minutes. On leaving the reactor, the reaction mixture was directly precipitated in 1 liter of 5% sulfuric acid. To remove unconverted chlorobenzene, this was distilled off azeotropically with water and the suspension was cooled to room temperature. The product was filtered off and washed twice with 500 ml of water each time and then dried. There were thus obtained 164 g (57%) of bis(4-chlorophenyl) sulfone showing a purity of 97%.

Example 2

A vertical glass tube having a length of 90 cm and a diameter of 4 cm was packed with glass balls and heated at 70° C. 225 g (2.0 moles) of chlorobenzene, 126 g (1.0 mole) of dimethyl sulfate and 160 g (2.0 moles) of sulfur trioxide were simultaneously fed, dropwise, to the top of the tube at approximately the same rates over 30 minutes. Contrary to the procedure adopted in Example 1, the effluent reaction mixture was not immediately precipitated in dilute sulfuric acid but was continuously recycled to the packed column at a pump rate of 2 l/h. Once all of the starting components had been fed to the reactor, recycling was continued at the same rate for a further half-hour, after which the effluent reaction mixture was precipitated in 1 liter of 5% sulfuric acid. Purification was carried out as described in Example 1 to give 261 g (91%) of bis(4-chlorophenyl) sulfone of 97% purity.

Example 3

Example 2 was repeated except that the reaction mixture was precipitated i 500 ml of chlorobenzene instead of dilute sulfuric acid. The precipitation medium was cooled to room temperature and the product was filtered off and washed twice with 200 ml of methanol each time. The dried product comprised 235.3 g (82%) of bis(4-chlorophenyl) sulfone showing a purity of >99.5%.

Example 4

126 g (1.0 mole) of dimethyl sulfate and 160 g (2.0 moles) of sulfur trioxide were fed at approximately equal rates to a packed reactor of the type described in Example 1 over a period of 30 minutes. The effluent reaction mixture was directly fed to a second packed reactor having the same dimensions and heated at 70° C., together with 225 g (2.0 moles) of chlorobenzene, these two components being fed at approximately the same rates, over a period of 30 minutes. The effluent mixture was continuously recycled to the inlet of the second reactor. Following a post-reaction time of 30 minutes, the effluent mixture was precipitated in 500 ml of 5% sulfuric acid and the precipitate was filtered off and washed twice with 500 ml of water and dried. There were thus obtained 223.9 g (78%) of bis(4-chlorophenyl) sulfone of 97% purity.

Example 5

Example 1 was repeated except that sintered boric acid balls of 4 mm in diameter were used as packing elements instead of glass balls. The product was worked up and dried in conventional manner to give 187 g (65%) of bis(4-chlorophenyl) sulfone showing a purity of 99%.

We claim:

1. A process for the preparation of bis (4-chlorophenyl) sulfone which comprises:
   simultaneously introducing and reacting in a single stage the reactants
   (a) sulfur trioxide,
   (b) dimethyl sulfate and
   (c) chlorobenzene
   in a molar ratio of (a):(b):(c) of from 0.1:0.005:1 to 2:1:1 and at a temperature of from 50° to 100° C.

2. A process as claimed in claim 1, wherein the reaction is carried out at from 70° to 90° C.

3. A process as claimed in claim 1, wherein sulfur trioxide, dimethyl sulfate and chlorobenzene are reacted in a molar ratio of from 0.1:0.05:1 to 1.5:0.8:1.

4. A process as claimed in claim 1, wherein sulfur trioxide, dimethyl sulfate and chlorobenzene are reacted in a molar ratio of from 0.5:0.25:1 to 1.1:0.6:1.

5. A process as claimed in claim 1, wherein sulfur trioxide, dimethyl sulfate and chlorobenzene are reacted in a molar ratio of from 1:0.5:1.

6. A process as claimed in claim 1, wherein the effluent reaction mixture from said single stage is recycled to said single stage to increase the residence time.

7. A process as claimed in claim 1, wherein the reaction is carried out continuously in a single stage.

8. A process as claimed in claim 1, wherein the reaction is carried out in a single stage reactor containing packing elements having a geometry, particle size and density selected to adjust the residence time of the reactants.

9. A process as claimed in claim 1, wherein the reaction is carried out in the presence of an acidic catalyst.

10. A process as claimed in claim 9, wherein the catalyst is boric acid.